US012684482B2

(12) United States Patent (10) Patent No.: US 12,684,482 B2 von Arx et al. (45) Date of Patent: Jul. 14, 2026

(54) METHOD FOR WAKING UP AN IMPLANTABLE MEDICAL DEVICE FROM A DORMANT STATE

(71) Applicant: BIOTRONIK SE & Co. KG, Berlin (DE)

(72) Inventors: Jeffrey A. von Arx, Lake Oswego, OR (US); Alan Fryer, Portland, OR (US); Richard Helvick, Portland, OR (US); Yu Wang, Lake Oswego, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 300 days.

(21) Appl. No.: 18/558,848

(22) PCT Filed: May 9, 2022

(86) PCT No.: PCT/EP2022/062412

§ 371 (c)(1),
(2) Date: Nov. 3, 2023

(87) PCT Pub. No.: WO2022/248199

PCT Pub. Date: Dec. 1, 2022

(65) Prior Publication Data

US 2024/0236854 A1 Jul. 11, 2024

Related U.S. Application Data

(60) Provisional application No. 63/193,294, filed on May 26, 2021.

(30) Foreign Application Priority Data

Jul. 1, 2021 (EP) ..................................... 21183022

(51) Int. Cl.
| | |
|---|---|
| *H04W 52/02* | (2009.01) |
| *A61N 1/362* | (2006.01) |
| *A61N 1/372* | (2006.01) |

(52) U.S. Cl.
CPC ........ *H04W 52/0229* (2013.01); *A61N 1/362* (2013.01); *A61N 1/37276* (2013.01)

(58) Field of Classification Search
CPC H04W 52/0229; A61N 1/362; A61N 1/37276
See application file for complete search history.

(56) References Cited

U.S. PATENT DOCUMENTS

| | | | | |
|---|---|---|---|---|
| 2007/0061805 | A1* | 3/2007 | Brenner | .................. G06F 9/485 |
| 2009/0252042 | A1 | 10/2009 | Bradley et al. | |

(Continued)

OTHER PUBLICATIONS

International Search Report (PCT/ISA/210) with translation mailed on Jul. 11, 2022, by the European Patent Office as the International Searching Authority for International Application No. PCT/EP2022/062412. (9 pages).

*Primary Examiner* — Ronald B Abelson

(74) *Attorney, Agent, or Firm* — Buchanan Ingersoll & Rooney PC

(57) ABSTRACT

A method for waking up an implantable medical device from a dormant state comprises: sending a wake-up signal via a wireless link by means of an external device; receiving the wake-up signal by the implantable medical device in the dormant state; activating an awake state of the implantable medical device in response to the wake-up signal; attempting with at least one or a predefined number of attempts, in the awake state of the implantable medical device, to establish a communication between the external device and the implantable medical device; identifying, by the implantable medical device, the activation of the awake state as a valid activation based on the attempting to establish a communication; and in case the activation of the awake state is not (Continued)

identified as a valid activation, blocking a subsequent acti-
vation of the awake state of the implantable medical device
based on the wake-up signal.

13 Claims, 4 Drawing Sheets

(56)                References Cited

U.S. PATENT DOCUMENTS

2009/0291656  A1    11/2009  Le et al.
2015/0065047  A1     3/2015  Wu et al.
2020/0129773  A1     4/2020  Eisele et al.
2020/0261733  A1     8/2020  Wang et al.

* cited by examiner

METHOD FOR WAKING UP AN IMPLANTABLE MEDICAL DEVICE FROM A DORMANT STATE

CROSS-REFERENCE TO RELATED APPLICATIONS

This application is the United States National Phase under 35 U.S.C. § 371 of PCT International Patent Application No. PCT/EP2022/062412, filed on May 9, 2022, which claims the benefit of European Patent Application No. 21183022.9, filed on Jul. 1, 2021, and U.S. Provisional Patent Application No. 63/193,294, filed on May 26, 2021, the disclosures of which are hereby incorporated by reference herein in their entireties.

TECHNICAL FIELD

The instant invention generally relates to a method for waking up an implantable medical device from a dormant state. The instant invention also relates to an implantable medical device as well as to a system comprising such an implantable medical device and an external device.

BACKGROUND

The function of an implantable medical device, such as, e.g., an implantable recording device such as a loop recorder, a sensor device such as an implantable pressure sensor, an implantable pulse generator of a cardiac pacemaker, is usually constrained by battery life. Therefore, RF transceivers of implantable medical devices are typically kept in a dormant state over extended periods to conserve power. Any wireless communication session with an external device therefore requires a method of waking up the device's RF transceiver. In this context, it is generally desirable that an implant circuitry uses a minimal amount of power, especially if false alarms (i.e., unintended wake-up events) can be expected. Further, a reliable authentication is needed to ensure that the device is woken up only by the proper external device. As a result of a valid authentication, the implantable medical device will be woken up, i.e., put in a communications state exhibiting an increased power consumption.

Existing solutions for waking up an implantable medical device rely, for example, on an inductive coil communication, wherein an inductive wand is placed within a few centimeters of the device to wake it up. Such methods require the inductive wand to be placed in close proximity (less than about 5 cm) of the implantable medical device.

In another existing approach, a static magnetic field of a magnet is used for initiating communication with an implanted medical device. This wake-up method has the inconvenience that it requires additional hardware and may hinder another magnet mode of the implantable medical device (e.g. a therapy or auto-MRI mode).

A further known solution is based on dedicated external RF hardware that generates a proprietary wake-up message (e.g., in the 900 MHz ISM band). This proprietary wake-up message would be specifically designed to be detectable with a very low power receiver in the implant. However, the wake-up via custom-made external hardware requires the design, fabrication and distribution of the external hardware, which is generally costly. In such an approach, hardware support functions will also be required.

Yet another approach provides for a periodic wake-up of an RF receiver of an implantable medical device and a decoding of a wake-up message. For example, U.S. Publication No. 2015/0065047 A1 discloses turning an external communication device into an advertising device for an implantable medical device. The implantable medical device comprises an RF detector circuit. It is proposed to use the Bluetooth standard for communication between the implantable medical device and the external device (e.g., a smartphone). The implantable medical device regularly performs a scan sequence in which it searches for a Bluetooth advertising signal from the external device. If an advertising signal from the external device is detected, a communication connection between implantable medical device and external device is established. This solution may, for example, utilize the Bluetooth capability of a smartphone used as an external device. However, the implantable medical device needs to periodically perform an RF (e.g., Bluetooth) receiver sniffing in order to detect and decode the advertising message from the smartphone. As a result, this known wake-up method still consumes a relatively high amount of battery power. In addition, the wake-up may be relatively slow depending on the period between consecutive RF receiver sniffing sequences.

U.S. Publication No. 2020/0129773 A1 discloses a method for facilitating communication between an implantable device and an external device, the method comprising broadcasting, via communication circuitry of an implantable medical device, a first set of advertisements at a first advertising rate according to a communication protocol. The method further comprises determining that detection circuitry of the implantable device detected voltage induced by an electromagnetic field at an interface between tissue of a patient and electrodes of the implantable device and in response to the detection of voltage induced by the electromagnetic field, broadcasting, via the communication circuitry, a second set of advertisements at a second advertising rate according to the communication protocol.

U.S. Publication No. 2020/0261733 A1, whose contents shall be incorporated by reference herein, discloses a method for waking up an implantable medical device from a dormant state in which an external device transmits a modulated wake-up signal via a wireless link. The modulated wake-up signal is received by the implantable medical device, which then demodulates the wake-up signal so as to produce a demodulated wake-up signal. Demodulator circuitry of the implantable medical device herein is permanently ready for operation. In response to the demodulated wake-up signal, an awake the state of the implantable medical device is activated.

In the scheme of U.S. Publication No. 2020/0261733 A1 an external device, for example in the shape of a regular, off-the-shelf mobile device such as a smart phone, may be used to wake up an implantable medical device. The external device herein transmits a modulated wake-up signal having the shape, e.g., of an advertising sequence as defined in a Bluetooth protocol, for example a Bluetooth Low Energy (BLE) protocol. The modulated wake-up signal may be demodulated and recognized by the implantable medical device, such that upon demodulation of the wake-up signal the implantable medical device is woken up in order to establish a communication with the external device. As reception circuitry, including in particular demodulator circuitry, can be designed to consume very limited power, the implantable medical device overall may exhibit a small power consumption, allowing for a prolonged duration of operation in an implanted state of the device.

Generally, an advertising sequence in a Bluetooth protocol usable to wake up the implantable medical device may be designed such that it is differentiated from common advertising sequences as used in a standardized Bluetooth protocol for establishing a communication using Bluetooth. In particular, pulse durations (the so-called PDU length) and a repetition interval within an advertising sequence may be adapted to define a specified advertising sequence which may be transmitted as a wake-up signal.

Generally, an implantable medical device will exhibit an increased power consumption if it is falsely woken up repeatedly, as each activation of the implantable medical device requires power. It hence needs to be avoided that an external device, such as a smart phone regularly using standardized communication techniques such as Bluetooth, may be able to unintentionally and repeatedly wake up an implantable medical device, for example because a signal transmitted by an external device is mistaken by the implantable medical device as a wake-up signal. Situations in which a signal by an external device repeatedly is interpreted (falsely) as a wake-up signal, leading to a repeated activation of the implantable medical device, may cause a wear down of the device's battery and hence a shortening of the operational life span of the device.

The present disclosure is directed toward overcoming one or more of the above-mentioned problems, though not necessarily limited to embodiments that do.

SUMMARY

It is an object of the present invention to provide a method for waking up an implantable medical device from a dormant state, an implantable medical device and a system including an external device and an implantable medical device which allow to prevent an excessive wear down of the implantable medical device's battery due to an unintentional waking of the implantable medical device.

In one aspect, a method for waking up an implantable medical device from a dormant state comprises: sending a wake-up signal via a wireless link by means of an external device; receiving the wake-up signal by the implantable medical device in the dormant state; activating an awake state of the implantable medical device in response to the wake-up signal: attempting with at least one or a predefined number of attempts, in the awake state of the implantable medical device, to establish a communication between the external device and the implantable medical device: identifying, by the implantable medical device, the activation of the awake state as a valid activation based on the attempting to establish a communication; and, in case the activation of the awake state is not identified as a valid activation, blocking a subsequent activation of the waking state of the implantable medical device based on the wake-up signal.

The predefined number of attempts may be 1, 2, 3 or higher than 3.

Within the method, in particular a regular, off-the-shelf mobile device, such as a smart phone, may be used as an external device. The external device may in particular implement communication techniques according to standardized communication protocols, such as Bluetooth, in particular Bluetooth Low Energy.

For waking up the implantable medical device, the external device is configured to transmit a wake-up signal which is constructed, for example, according to an advertising sequence as it is applicable within a communication technique such as Bluetooth, in particular Bluetooth Low Energy. Within such an advertising sequence, advertising packets (so-called PDUs) may be used to broadcast data, the advertising sequence being received by the implantable medical device and being processed in order to identify the advertising sequence as a valid wake-up signal to cause a waking of the implantable medical device.

For waking the implantable medical device, an awake state of the implantable medical device is activated in response to receiving a (valid) wake-up signal. The awake state herein may correspond to a state in which the implantable medical device is fully operational, such that processing modules of the device are active. In another embodiment, the awake state may correspond to a state in which communication circuitry of the implantable medical device is active, but further components, such as a sensing circuitry or stimulation circuitry of the device, are not necessarily active, but are, for example, switched on only after verifying that the activation is truly based on a wake-up signal transmitted from an external device with the intent to wake-up the implantable medical device.

In response to the activation of the awake state of the implantable medical device, the implantable medical device attempts to establish a communication with the external device. Within Bluetooth this, for example, may take place in that the implantable medical device transmits an advertising sequence in response to the advertising sequence as received from the external device, upon which the external device transmits a so-called scan request, which is responded to by the implantable medical device in a so-called scan response. Once communication is established, e.g., according to the Bluetooth technique or according to another technology such as telemetry, data may be exchanged in between the external device and the implantable medical device.

If, during the attempt to establish a communication, it is found that the external device erroneously woke up the implantable medical device, for example by transmitting a signal which is close to a specified wake-up signal, such as an advertising sequence according to the Bluetooth scheme, the implantable medical device identifies the activation of the awake state as invalid and, for example, terminates the communication with the implantable medical device.

For example, an external device equipped to wake up the implantable medical device may use a specialized software (such as a so-called app installed on the external device) to wake up the device and to establish a communication. During establishment of the communication the external device may have to identify itself towards the implantable medical device or may be required to transmit specified information to the implantable medical device. If the external device is not able to identify itself, or does not adhere to a prescribed sequence of data exchange as expected by the implantable medical device, the implantable medical device may identify the external device as not authorized to establish communication with the implantable medical device, such that the activation of the awake state is found to be invalid.

In case it is found that the activation of the awake state of the implantable medical device has been found to be not valid, a future activation caused by the particular wake-up signal which has led to the (false) activation of the implantable medical device shall be prevented. For this, a subsequent activation of the awake state of the implantable medical device based on the wake-up signal is blocked, such that the implantable medical device is not woken up again if the external device keeps repeating a signal which previously has been mistaken as a wake-up signal.

In one embodiment, the implantable medical device may block an activation of the awake state based on the wake-up signal after a first reception of the particular wake-up signal, such that after the first reception of the wake-up signal and the identification of the activation of the awake state as invalid following the reception of the wake-up signal a further activation based on the wake-up signal is blocked.

In another embodiment, the implantable medical device may block an activation of the awake state based on the wake-up signal only if the implantable medical device receives the particular wake-up signal repeatedly. E.g., the implantable medical device may block an activation based on the particular wake-up signal only if the number of receptions of the wake-up signal in a predefined time span exceeds a predefined number, for example 2, 3, 4 or more receptions of the wake-up signal. The predefined time span may, for example, have a duration of multiple minutes, for example between 5 minutes and 20 minutes. If the particular wake-up signal in the predefined interval is received multiple times, causing a repeated activation of the implantable medical device, the particular wake-up signal is blocked, such that a further reception of a signal resembling that wake-up signal will not cause an activation of the awake state of the implantable medical device.

In one embodiment, the step of receiving by the implantable medical device includes the processing of the wake-up signal to identify the wake-up signal as a valid wake-up signal. For example, for verifying the wake-up signal as a valid signal the wake-up signal may be compared to a predefined matching signal, for example by deriving information from the wake-up signal in order to compare the information to a predefined set of information characteristic of the matching signal to identify the wake-up signal as a valid wake-up signal.

Generally, herein, a wake-up signal is that (e.g., RF) signal which is transmitted by the external device and received by the implantable medical device. The wake-up signal is verified with respect to a predefined matching signal, wherein the wake-up signal is assumed to be valid if the wake-up signal according to certain criteria is found to match the matching signal. In that case the awake state is activated. If no match between the wake-up signal and the predefined matching signal is found, no valid wake-up signal is assumed to be present, and no activation of the awake state takes place.

If, for example, an advertising sequence according to Bluetooth, in particular Bluetooth Low Energy, is used as the wake-up signal, the wake-up signal may be constructed of a number of transmission pulses (so-called PDUs), which, for example, may be sent on a single or on multiple Bluetooth channels. Groups of transmission pulses herein may be repeated at a predefined interval, such that the advertising sequence assumes a periodic shape, in which the transmission pulses may have equal or different pulse durations and are repeated groupwise according to a predefined advertising interval. Information which may be derived from the advertising sequence, hence, may relate to pulse durations of the transmission pulses, and an interval used for the periodic transmission of the groups of transmission pulses.

In one embodiment, multiple matching signals may be predefined and may be usable by the external device to wake-up the implantable medical device. For example, the wake-up signal may be identified as a valid wake-up signal if the derived information matches a predefined set of information out of a multiplicity of sets of information representative of a group of predefined matching signals. Each matching signal of the group of predefined matching signals may, for example, be characterized by a certain characteristic set of information, for example a combination of pulses of certain pulse durations which are repeated at a particular interval characteristic for the matching signal. As multiple matching signals are defined, an external device may use a wake-up signal corresponding to one out of multiple matching signals to wake up the implantable medical device. If a wake-up signal according to any of the valid, predefined matching signals is received by the implantable medical device, the implantable medical device identifies the received signal as a valid wake-up signal and correspondingly activates the awake state.

In one embodiment, the blocking of a particular wake-up signal includes the step of preventing an activation of the awake state of the implantable medical device based on the wake-up signal for a predefined time duration. Hence, the particular wake-up signal, for which the activation of the awake state has been found to be not valid, is not blocked for all times, but only for a predefined time duration. After lapse of the time duration a reception of the particular wake-up signal may again lead to an activation of the awake state and hence to a waking of the implantable medical device.

In one embodiment, the step of blocking includes marking a predefined matching signal corresponding to the wake-up signal as invalid in a list of matching signals. The list may be assumed to be a blocklist indicating such matching signals which have been found previously to lead to an invalid activation of the implantable medical device. In particular in case that multiple matching signals are available to cause an activation of the awake state of the implantable medical device, a particular matching signal may be blocklisted such that it is no longer usable for waking up the implantable medical device. If subsequently a signal is received by the implantable medical device which resembles a matching signal as identified in the blocklist (i.e., in the list of matching signals), the implantable medical device is not transferred to its awake state and hence is not activated.

Thus, in one embodiment, the blocking includes: marking a predefined matching signal corresponding to the wake-up signal as invalid in a list of matching signals so that a signal is received by the implantable medical device which resembles a matching signal as identified in the list of matching signals, the implantable medical device is not transferred to the awake state.

In an unlikely event it may occur that the number of predefined matching signals (defining wake-up signals usable for waking up the implantable medical device) marked as invalid in the list of matching signals becomes large (for example, if all predefined matching signals are included in the list), such that a reliable waking of the implantable device may no longer be possible, or a waking may not be possible at all. For this reason, in one embodiment the list of matching signals may be modified in case it is detected that the list of matching signals includes a number of matching signals equal to or exceeding a predefined maximum number. The maximum number may, for example, correspond to a substantial amount of all the available matching signals, for example 50% or more of the available matching signals. In one embodiment, the maximum number corresponds to the number of all available matching signals, such that the list is only modified if it is found that all available matching signals are included in the list.

For modifying the list, for example one or multiple matching signals may be removed from the list by marking the one or the multiple matching signals again (again) as valid. Hence, following the modification of the list, the particular matching signal(s) is (are) again usable for waking up the implantable medical device, such that in case a wake-up signal is received by the implantable medical device which resembles a matching signal no longer included in the list the implantable medical device is activated to assume its awake state.

For removing one or multiple matching signals from the list, for example a first on/first of scheme may be used, such that that matching signal is removed first from the list which has first been introduced into the list. In another approach, one or multiple matching signals may randomly be removed from the list and hence may be marked again as valid.

In one embodiment, alternatively or in addition to modifying the blocklist of matching signals, a time duration for which all or at least a subgroup of the matching signals are kept on the list may be modified. For example, if it is detected that the list of matching signals includes a number of wake-up signals equal to or exceeding a predefined maximum number, a value of a predefined time duration, during which an activation of the awake state of the implantable medical device is blocked for a particular matching signal, may be decreased for at least one matching signal of the list of matching signals. Hence, a blocking time is shortened. This may be applied to all the matching signals included in the list, or to a subgroup of matching signals on the list. A subgroup may, for example, be chosen randomly, or on a first on/first off basis.

In one embodiment, the external device is configured to send a modulated wake-up signal via the wireless link by means of an external device. For example, the external device may comprise a Bluetooth interface by means of which the wake-up signal is transmitted, the wake-up signal, for example, having the shape of an advertising sequence according to the Bluetooth technique. Herein, wherein the general scheme of the advertising sequence may be defined in the Bluetooth protocol, certain parameters of the advertising sequence such as pulse durations or a repetition (advertising) interval may be adapted by a software on the external device in order to define a specific wake-up signal usable for waking up the implantable medical device.

In one embodiment, the implantable medical device comprises demodulator circuitry configured to demodulate the wake-up signal so as to produce a demodulated wake-up signal, wherein the demodulator circuitry preferably is permanently ready for operation. Hence, a wake-up procedure is initiated by means of a modulated wake-up signal transmitted by the external device. The wake-up signal is demodulated by means of the demodulator circuitry of the implantable medical device, wherein the demodulator circuitry is beneficially permanently ready for operation (always on). Advantageously, with this solution, the implantable medical device itself does not need to actively scan for a wake-up signal. Instead, the external device emits a modulated signal, which in one embodiment is detected by the demodulator passively. Due to the omission of scanning, a fast and low-energy wake-up process is achieved. In other words, the always-on demodulator circuitry eliminates the need for a periodical scan (such as a periodical RF sniff) of the implanted medical device, resulting in power saving and a shortened latency for the wake-up.

In an embodiment, the implantable medical device comprises a communications transceiver circuitry being configured to support a wireless communication with the external device in the awake state. For example, the wireless communication may use an RF link. The wireless communication may be carried out according to an established communication standard, such as, e.g., Bluetooth.

Further, the communications transceiver circuitry may be configured to assume a low-power-consumption mode in the dormant state of the implantable medical device. The communications transceiver circuitry may be inactive in the low-power-consumption mode. For example, a wireless communication between the communications transceiver circuitry of the implantable medical device and the external device may thus not be supported in the dormant state. Upon activating the awake state (and thereby exiting the dormant state), the implantable medical device may power up the communications transceiver for enabling a user communication, e.g., a telemetry session.

It shall be noted herein that the communication of the implantable medical device may take place using a communication technology as it also is used for waking up the implantable medical device. This however is not necessarily required. If, for example, is possible that the waking of the implantable medical device takes place by an advertising sequence transmitted by the external device using, e.g., the Bluetooth technology, wherein subsequently a communication in between the implantable medical device and the external device is established according to another communication technique, for example a telemetry technique.

In one embodiment, the modulated wake-up signal is an amplitude modulated signal, such as, e.g., a signal modulated by means of amplitude shift keying (ASK). Correspondingly, in an embodiment, the demodulator circuitry may be an amplitude demodulator circuitry, such as an ASK demodulator circuitry. For example, in such an embodiment, a payload of the wake-up message may not be important and will not be decoded. Instead, an RF amplitude change in the time domain may be indicative of a valid wake-up request. This may be beneficial in terms of privacy protection, since no private information is used for wake-up and/or authentication.

BLE uses Gaussian Frequency Shift Keying (GFSK) to encode bits, not ASK. However, the low frequency envelope of the BLE advertising packets and the quite between advertising packets can be detected as logical 1s and 0s by a low power ASK receiver. Key parameters that the ASK receiver would detect is the duration of the advertising packet, and the duration of the interval between advertising packets, both of which can be set to make a unique ASK wake up signal.

Further, in one embodiment, the demodulator circuitry may be implemented as a zero-power-consumption demodulator circuitry, e.g., in the form of a zero-power-consumption RF envelope ASK demodulator. Employing such a zero-power-consumption ASK demodulator, which is permanently ready to receive, may eliminate the need to periodically turn on a receiver (such as a Bluetooth receiver) to decode potentially incoming advertising/wake-up packets. This may result in significant power saving for the implantable medical device.

For example, such an ASK demodulator circuitry may be implemented with an optimized envelope sensitivity to minimize false wake-up events. For example, a series inductor may be provided to accurately control an input impedance of the demodulator circuitry. Further, the ASK demodulator circuitry may be designed in such a way that it is capable of detecting a wake-up signal only in close proximity (e. g. up to several inches) to the external device from which the wake-up signal is transmitted. The required proximity and/or the optimized envelope sensitivity add to the security of the pairing between the external device and the implantable medical device.

In an embodiment, the implantable medical device further comprises a match detector circuitry that is configured to validate the demodulated wake-up signal (e.g., a baseband signal). For example, the match detector circuitry may be provided in the form of an ultra-low-power baseband detector circuitry, such as an ultra-low-power ASK match detector circuitry (in case the demodulator circuitry is an ASK demodulator circuitry). The ASK match detector circuitry is configured to receive the demodulated wake-up signal from the ASK demodulator circuitry, to verify the received wake-up signal and to initiate a wake-up, i.e., the activation of the awake state, of the implantable medical device based on said verification. For example, the match detector circuitry recognizes a valid wake-up signal according to its amplitude and frequency.

In an embodiment, the implantable medical device comprises control circuitry, such as a baseband controller, that is configured to activate the awake state in response to the demodulated wake-up signal. For example, said control circuitry and the match detector circuitry are integrated in a baseband controller. Further, in an embodiment, the demodulator module may also be integrated in a baseband controller, e.g., together with said control circuitry and/or the match detector circuitry. In another embodiment, the demodulator circuitry may be provided separately from a baseband controller, e.g., as a discrete circuit.

The external device may function, for example, as a so-called patient remote. Additionally, the external device may function as an authentication device. In an embodiment, the external device is a mobile device, such as a smartphone. For example, the method according to the instant invention allows for using a commercial smartphone as an external secure wake-up/authentication device. The wake-up method shall be secure but portable, such that only a smartphone with customized software can be used to wake up the implant (preferably only at close proximity). It is convenient for a patient to unite the functionality of a patient remote and an authentication device in one smartphone. This alleviates the need for a separate patient activator (e.g., a magnet or inductive coil), since most patients already carry a smartphone. The patient may thus use a commercial smartphone as a secure patient activator to wake up the implantable medical device. Once paired with an implant, additional smartphone features may be employed. As a result, since no customized hardware external to the implantable medical device is needed, the system costs may be reduced.

In an embodiment, the external device is capable of generating the modulated wake-up signal in the form of a specific RF wake-up sequence, which may be, for example, specified by the vendor of the implantable medical device. A software of the external device that controls the wake-up protocol may also be capable of switching the external device from an advertising mode into a scan/connect mode according to a specific sequence. In other words, a commercially available external device, such as a smartphone, may be provided with customized software that controls the wake-up advertising sequence and the role switching from advertise to scan/connect.

Further, in an embodiment, the wake-up protocol may be compatible with an established communication standard, such as the Bluetooth protocol. Thus, in accordance with a preferred embodiment, the wake-up protocol is not covered by but compatible with the Bluetooth standard. For example, specific Bluetooth compatible advertising and/or extended advertising transmission sequences may be created. In an exemplary embodiment, a BLE 5.0 extended advertising sequence is used as a wake-up signal sequence. Hence, in accordance with some embodiments, the modulated wake-up signal may be transmitted via a Bluetooth interface of the external device.

In another aspect, an implantable medical device configured to selectively assume an awake state and a dormant state comprises: reception circuitry configured to receive a wake-up signal via a wireless link from an external device: activation circuitry configured to activate an awake state of the implantable medical device in response to a received wake-up signal: communication circuitry configured to establish, in the awake state, a communication between the external device and the implantable medical device: and processing circuitry configured to identify the activation of the awake state as a valid activation based on at least one or a predefined number of attempts to establish a communication, and in case the activation of the awake state is not identified as a valid activation, to block a subsequent activation of said awake state of the implantable medical device based on the wake-up signal.

In one embodiment, the communication circuitry is configured to establish a communication according to a Bluetooth protocol, in particular a Bluetooth Low Energy protocol, for example according to BLE 5.0.

In yet another aspect, a system comprises an external device configured to send a wake-up signal via a wireless link, and an implantable medical device configured to selectively assume an awake state and the dormant state. The implantable medical device comprises reception circuitry configured to receive a wake-up signal via a wireless link from the external device: activation circuitry configured to activate an awake state of the implantable medical device in response to a received wake-up signal: communication circuitry configured to establish, in the awake state, a communication between the external device and the implantable medical device: and processing circuitry configured to identify the activation of the awake state as a valid activation based on at least one or a predefined number of attempts to establish a communication, and in case the activation of the awake state is not identified as a valid activation, to block a subsequent activation of said awake state of the implantable medical device based on the wake-up signal.

The advantages and advantageous embodiments described above for the method equally apply to the implantable medical device and to the system, such that it shall be referred to the above in this respect. In particular, aspects described for the method equally apply also to the implantable medical device and to the system.

Employing a scheme like the one proposed herein may allow to define an implantable medical device having an extremely low power consumption. With the scheme proposed herein, the implantable medical device may be woken up on demand, i.e., not only during certain windows. The wake-up may take place with a small latency, for example smaller than 10 seconds. The waking up may be achieved with an external device, for example, in the shape of an off-the-shelf mobile device, such as a smart phone, requiring no additional hardware.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily understood with reference to the following detailed description and the exemplary embodiments shown in the drawings. Herein.

DETAILED DESCRIPTION

Figure 1:
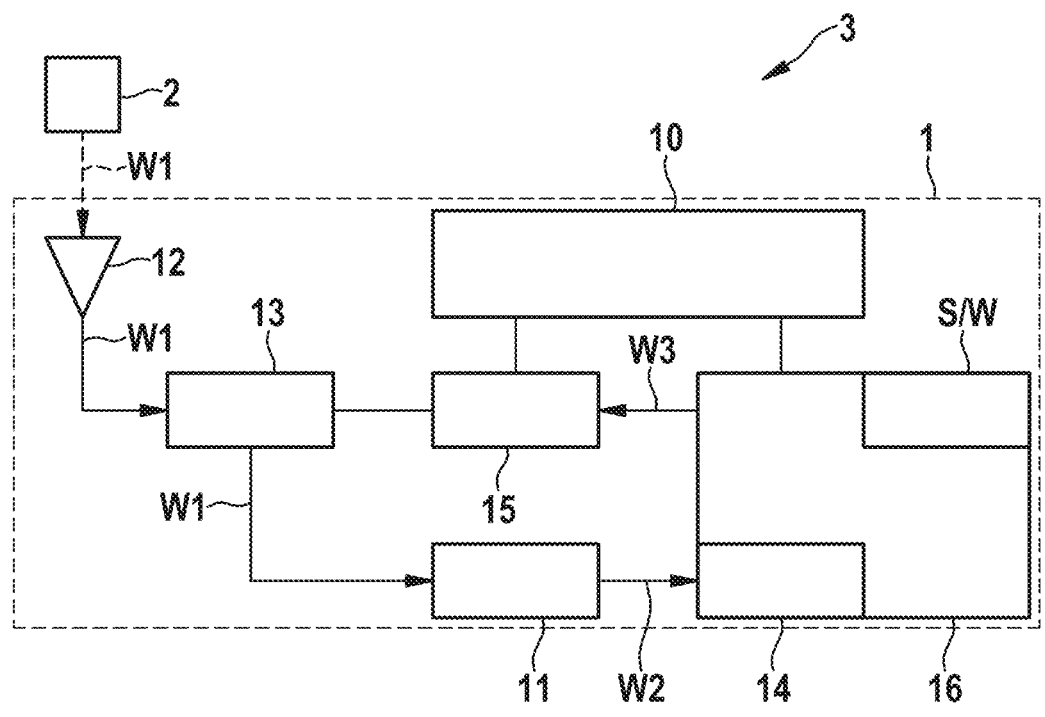
FIG. 1 shows a schematic view of a system comprising an implantable medical device and an external device.

In the following, embodiments of the present invention shall be described in detail with reference to the drawings. In the drawings, like reference numerals designate like structural elements.

It is to be noted that the embodiments are not limiting for the present invention, but merely represent illustrative examples.

FIG. 1 shows a schematic view of a system 3 comprising an implantable medical device 1 and an external device 2. In the present exemplary embodiment, the external device 2 is a smartphone that is used by a patient as a patient remote. The implantable medical device 1 may be or may comprise, for example, a recording device such as a loop recorder or a pulse generator of a cardiac pacemaker that is implanted in the patient's body.

In FIG. 1, a communications module of the implantable medical device 1 is depicted. Further components of the implantable medical device 1, such as, e.g., a memory, a therapy delivery unit, or other components, are not shown in FIG. 1 for simplicity.

The implantable medical device 1 comprises a communications transceiver circuitry 15, e.g., in the form of a Bluetooth chip, which is configured to support a wireless communication with the external device 2. Further, the implantable medical device 1 comprises a control circuitry 16, e.g., in the form of a baseband controller, which is connected to the communications transceiver circuitry 15. Both the communications transceiver circuitry 15 and the control circuitry 16 are connected to a power supply 10 of the implantable medical device 1.

The implantable medical device 1 is configured to selectively assume an awake state and a dormant state. In the awake state, the communications transceiver circuitry 15 is active so as to support the wireless communication with the external device 2. In the dormant state, the communications transceiver circuitry 15 (i.e., both transmitter and receiver) assumes a low-power-consumption mode, which does not support the wireless communication with the external device 2.

The external device 2 is configured to generate and send a modulated wake-up signal W1 via a wireless link (such as a Bluetooth link) so as to wake up the implantable medical device 1, i.e., trigger a transition of the implantable medical device 1 from its dormant state to its awake state. For example, to this end, the external device 2 comprises customized software that supports the generation of the modulated wake-up signal W1. The modulated wake-up signal W1 may be compatible with the Bluetooth standard. For example, the modulated wake-up signal W1 may take the form of a customized advertising sequence compatible with BLE 5.0. In the present embodiment, the modulated wake-up signal W1 is an amplitude shift keying (ASK) signal. In the embodiment where the wake-up signal is a customized BLE advertising sequence, it is the envelope of the advertising packet (a logical 1) and the delay between advertising packets (a logical 0) that makes up a very low frequency ASK wake up signal. BLE itself uses GFSK modulation that the ASK wake up receiver is unable to decode (because it would take much more power to implement a GFSK receiver). However, the ASK wake-up receiver can detect the envelope of the BLE advertising sequence and can limit its wake-ups to only certain envelope patterns.

The modulated wake-up signal W1 is received by an antenna 12 of the implantable medical device 1. The antenna 12 is connected to the communications transceiver circuitry 15 via a frontend matching circuitry 13. Thus, the antenna 12 is arranged and configured to support the wireless user communication with the external device 2 in the active state of the implantable medical device 1.

The frontend matching circuitry 13 is also connected to a demodulator circuitry 11, wherein the frontend matching circuitry 13 is installed upstream to the demodulator circuitry 11, i.e., between the antenna 12 and the demodulator circuitry 11. The frontend matching circuitry 13 is configured to receive and filter the modulated wake-up signal W1 before transmitting it to the demodulator circuitry 11. While the implantable medical device 1 is in the dormant state, the frontend matching circuitry 13 makes sure that an incoming modulated wake-up signal W1 is transmitted to the demodulator circuitry 11 instead of being transmitted to the communications transceiver circuitry 15. In one embodiment the wake-up signal goes to both the demodulator circuitry 11 and the communications transceiver circuitry 15, but since the transceiver circuitry 15 is in a dormant state, it ignores the signal.

Figure 2:
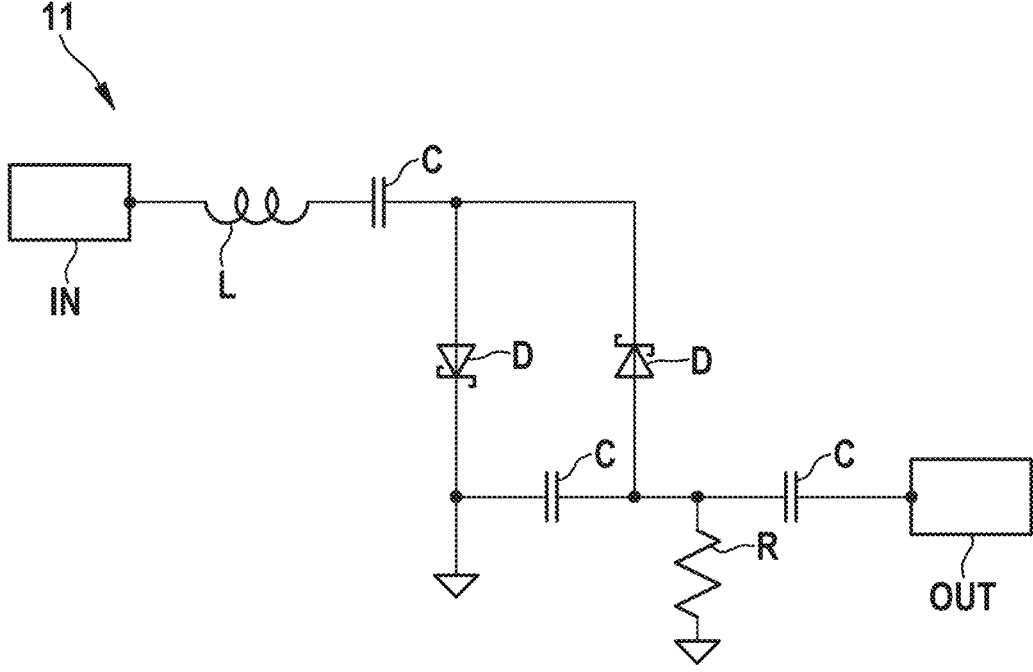
FIG. 2 schematically illustrates a demodulator circuitry.

In the present exemplary embodiment, the demodulator circuitry 11 is a zero-power-consumption ASK demodulator circuitry that is permanently ready to operate. An example of such an always-on, zero-power-consumption ASK demodulator 11 is illustrated in FIG. 2, which will be described in more detail further below.

The always-on ASK demodulator circuitry 11 is configured to demodulate the modulated wake-up signal W1 so as to generate a demodulated wake-up signal W2 (e.g., a baseband signal). For example, to this end, the ASK demodulator circuitry 11 is configured to extract an envelope of the modulated wake-up signal W1 so as to produce the demodulated wake-up signal W2. Even if the wake-up signal W1 is a GFSK encoded signal, such as is the case with BLE, the demodulator circuitry 11 will demodulate the envelop of packets/between packet interval as an ASK signal.

The demodulated wake-up signal W2 is subsequently transmitted to a match detector circuitry 14 that is configured to validate the demodulated wake-up signal W2. This is to say that the match detector circuitry 14 verifies the demodulated wake-up signal W2, wherein a valid wake-up signal W2 may be recognized according to its amplitude and frequency, for example. Hence, the match detector circuitry 14 may check that the signal from external device 2 is not (or is unlikely to be) random noise by verifying a valid wake-up signal W2.

The match detector circuitry 14 may be designed as an ultra-low-power baseband detector circuitry. In the present embodiment, the match detector circuitry 14 forms a part of the control circuitry 16 of the implantable medical device 1.

In other embodiments, the match detector circuitry 14 may be separate from the control circuitry 16.

The control circuitry 16 may comprise software S/W stored in one or more memory units as well as one or more processor units which are controlled by the software S/W. The control circuitry 16 activates the awake state in response to the detection of a valid wake-up signal W2 by means of the match detector circuitry 14. For example, to this end, the control circuitry 16 may transmit a logical wake-up signal W3 to the communications transceiver circuitry 15. In response to the logical wake-up signal W3, the communications transceiver circuitry 15 may be powered up so as to be able to support the wireless user communication with the external device 2. For example, after activating the awake state, a wireless communication session, such as a telemetry session, between the implantable medical device 1 and the external device 2 may be established.

FIG. 2 schematically illustrates a demodulator circuitry 11, which may be employed, for example, in the implantable medical device 1 of FIG. 1. The depicted layout, which comprises a number of diodes D and capacitors C as well as a resistor R and an inductor L, realizes a zero-power-consumption always on ASK demodulator 11. The illustrated ASK demodulator circuitry 11 provides an optimized envelope sensitivity to minimize false wake-up events. In particular, the series inductor L is provided to accurately control an input impedance of the ASK demodulator circuitry 11. For example, by means of the series inductor L, an appropriate trade-off between the demodulator circuitry 11 and the main RF path in FIG. 1 (i.e., the path to the communications transceiver circuitry 15) may be adjusted. The DC blocking cap at the output of the demodulator circuitry 11 shown in FIG. 2 is provided for enabling a bias independent interface with match detector circuitry 14.

According to an embodiment, the DC blocking cap allows the ASK waveform to be detected by the IP block that were implemented based on U.S. Pat. No. 8,428,528 B2 (See, for example, the baseband filtering and amplification unit 308 in FIG. 3 of said reference).

An ASK demodulator circuitry 11 such as the one that is exemplarily shown in FIG. 2 may be provided as a discrete circuitry or as an integrated circuit (e.g., based on the CMOS semiconductor fabrication technology). For example, in the latter case, the demodulator circuitry 11 may be integrated into the control circuitry 16, here in form of a baseband controller 16. In that case, the baseband controller 16 must exhibit an analog input port capable of receiving an RF signal.

Figure 3:
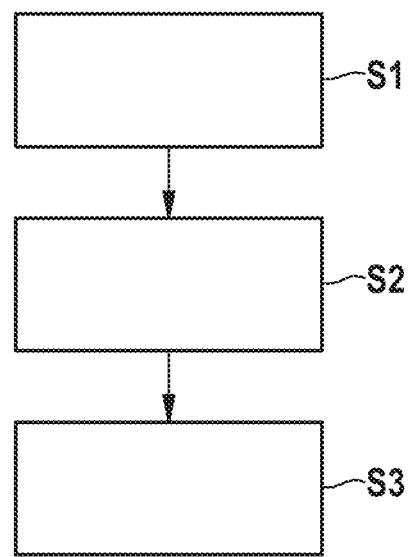
FIG. 3 is a schematic representation of the method according to the instant invention in the form of a block diagram.

FIG. 3 illustrates a wake-up method in a schematic block diagram. In a first step S1, the modulated wake-up signal W1 is transmitted by the external device 2 via the wireless link (e.g., Bluetooth). In a second step S2, the modulated wake-up signal W1 is demodulated and a demodulated wake-up signal W2 is thus generated by means of the zero-power-consumption or very low power consumption always on ASK demodulator circuitry 11. In a third step S3, the wake-up signal W2 is validated by the match detector circuit 14. Only if validation was successful, the awake state of the implantable medical device 1 is activated in response to demodulated wake-up signal W2. Further details and intermediate steps in accordance with one or more embodiments have been addressed above and will be addressed in the following.

Figure 4:
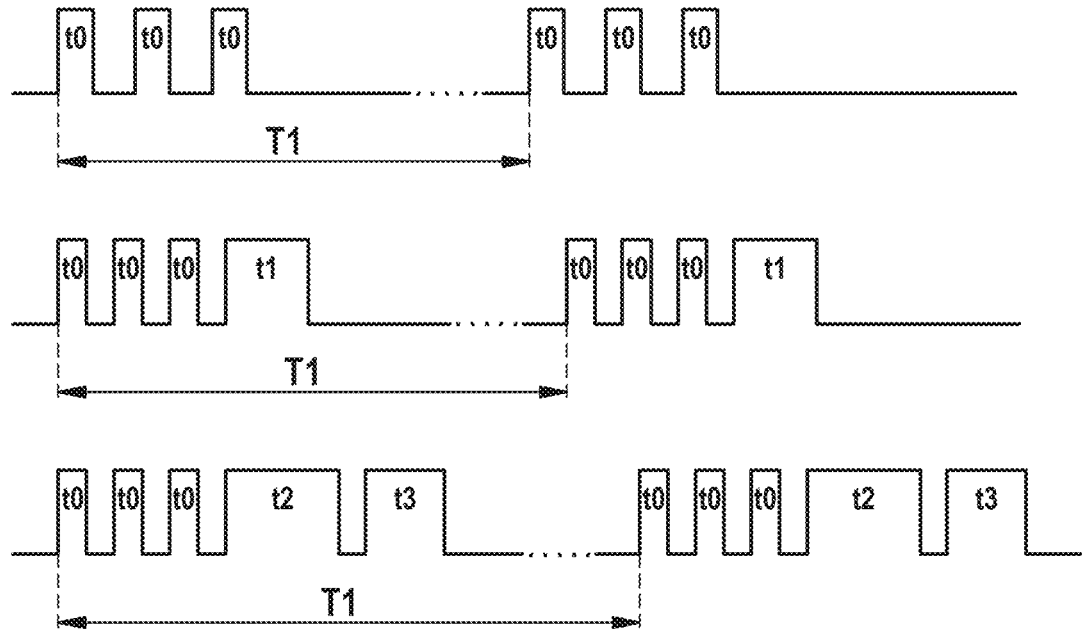
FIG. 4 schematically illustrates possible RF wake-up sequences for BLE devices.

FIG. 4 schematically illustrates possible RF wake-up sequences for Bluetooth Low Energy (e.g., BLE5) devices. Such wake-up sequences may be generated by the external device 2 by means of appropriate software. For example, the wake-up sequences may be generated in the form of customized (vendor-specific) Bluetooth advertising sequences. While the BLE signal itself encodes data with GFSK modulation, the envelope of packets and time between packets makes an ASK signal. As illustrated, such signal sequences are characterized essentially by a sequence of pulse groups having a period/interval T1 and using pulses (also denoted as PDUs, for Packet Date Units) having pulse durations t0, t1, t2, t3. These parameters T1, t0, t1, t2, t3 may be controlled at least to a certain degree by means of software, which may be provided by the external device 2 vendor (assuming the external device 2 is an 'off the shelf' device). It should be noted that the exemplary wake-up sequences shown in FIG. 4 yet have to be ASK modulated to form the modulated wake-up signal W1. In other words, the illustrated signal sequences may correspond to envelopes of the modulated wake-up signal W1, which may be reconstructed at the receiving end by means of the demodulator circuitry 11 of the implantable medical device 1.

In principle, the wake-up transmitter according to the present invention can use ASK, FSK or any other modulation as desired. In the case of BLE protocol, the actual RF wake-up sequence generated is GFSK modulated packets sequence hopping over multiple BLE RF channels.

The 'always on' ASK detector of the implant, according to one embodiment, detects the RF wake-up waveform and translates its envelope into a baseband ASK waveform. It then feeds the baseband ASK waveform to the baseband detector in order to find a match and trigger the wake-up of the main BLE transceiver.

Figures 5, 6:
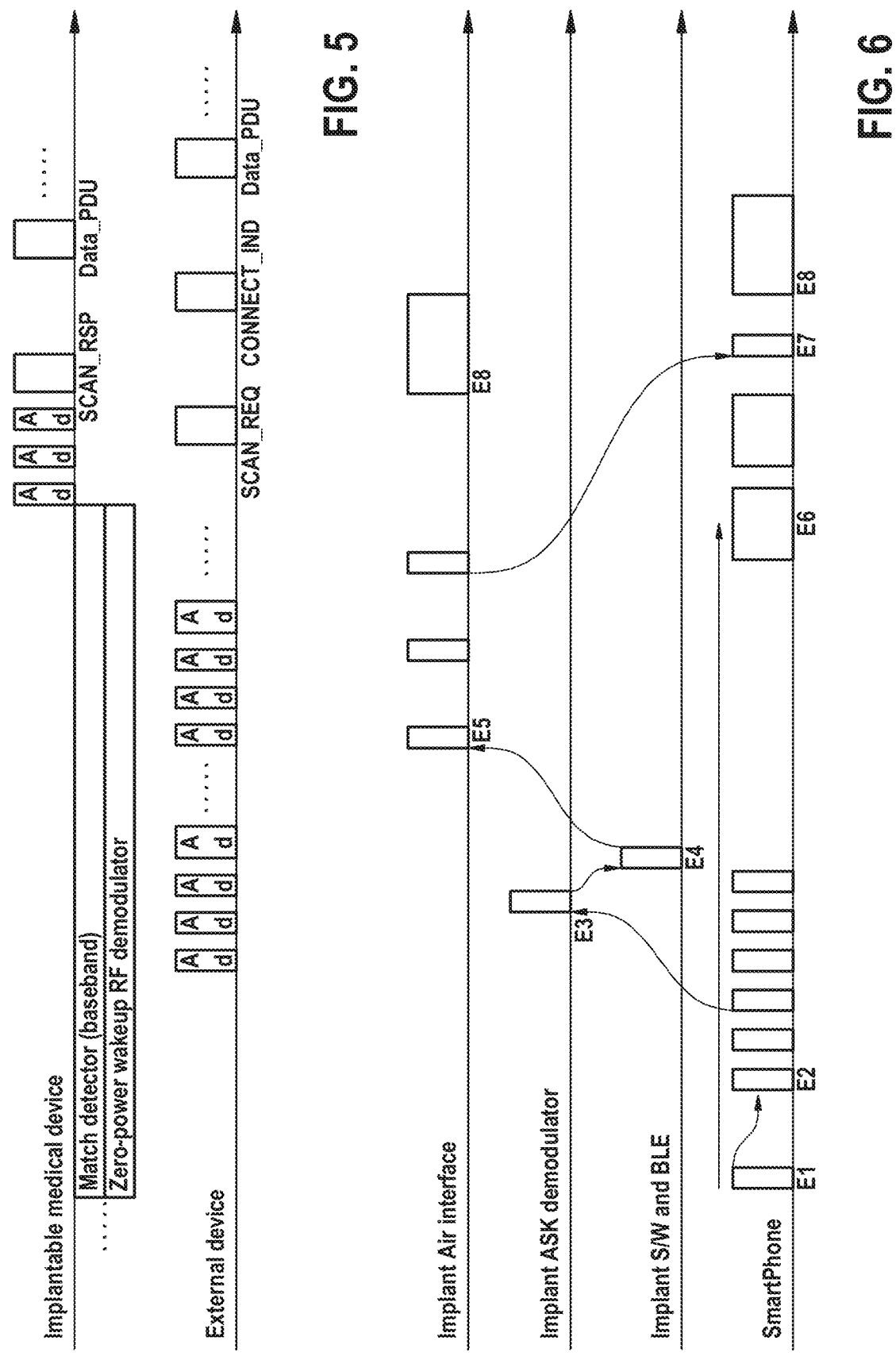
FIG. 5 schematically illustrates an exemplary wake-up protocol in accordance with one or more embodiments.
FIG. 6 schematically illustrates important events during a wake-up procedure in accordance with one or more embodiments.

FIG. 5 schematically illustrates an exemplary wake-up protocol in accordance with an embodiment. In this example, the wake-up protocol is based on a BLE5.0 extended advertising sequence that is used as the wake-up sequence.

Initially, the implantable medical device 1 is in the dormant state, wherein the communications transceiver circuitry 15 is inactive and only the demodulator circuitry 11 ("zero-power wake-up RF demodulator") and the match detector circuitry 14 ("Match detector (baseband)") are ready to operate.

Then, a communications transceiver of the external device 2 initiates a communication session, such as a telemetry session, with the implantable medical device 1. To this end, the external device 2 transmits an ASK modulated wake-up signal W1 that corresponds to a (customized) BLE5.0 extended advertising sequence. Such advertisement events are designated with the reference "Ad" in FIG. 5. Thus, in the present embodiment, a BLE portion of the wake-up protocol is driven by the external device 2.

The modulated wake-up signal W1 is received and processed by the implantable medical device 1 according to the procedure as described above with reference to FIGS. 1-4. As a result, the implantable medical device 1 activates its awake state.

After the activation of the awake mode, an advertising mode of the communications transceiver circuitry 15 of the implantable medical device 1 is activated (see reference "Ad" in the upper panel of FIG. 5). The external device 2 scans for an advertising package from the implantable medical device 1. Having received such an advertising package, the external device 2 sends a scan request ("SCAN_ REQ") to the implantable medical device 1. Subsequently, in a connection/service discovery phase, further messages ("SCAN_RSP", "CONNECT_IND", "DATA_PDU") are exchanged between the external device 2 and the implantable medical device 1 so as to perform a handshake according to the standard.

FIG. 6 schematically and exemplarily illustrates events E1-E8 that occur during a wake-up procedure in accordance with the embodiment described above with reference to FIG. 5.

At the outset of the wake-up procedure, the external device 2 ("SmartPhone") starts a wake-up request event E1. Subsequently, the external device 2 starts sending an advertising message who's envelop is in the form of an ASK modulated wake-up signal W1, wherein no private information is sent with the advertising message (event E2).

At event E3, the demodulator circuitry 11 of the implantable medical device 1 ("Implant ASK demodulator") demodulates the RF amplitude of the modulated signal W1 and passes the amplitude waveform (i.e., the demodulated wake-up signal W2) to the match detector circuitry 14 ("Implant S/W and BLE"). The match detector circuitry 14 confirms that a valid wake-up sequence has been received, thereby authenticating and/or verifying the external device 2 (event E4). Next, the Bluetooth communications transceiver circuitry 15 ("Implant Air interface") of the implantable medical device 1 is set into an advertising mode (event E5). The external device 2 transitions to a scan mode after a programmable time as measured from the wake-up request (event E6).

Having received an advertising package sent by the implantable medical device 1, the external device 2 sends a scan request to the implantable medical device 1 (event E7). Subsequently, the external device 2 and the implantable medical device 1 enter into a connection/service discovery phase and perform the necessary handshake according to the standard (event E8).

It should be noted that in this exemplary embodiment of a wake-up procedure, the implantable medical device 1 potentially never enters into a scan mode, but may establish a communication according to another communication technique, e.g., telemetry.

Figure 7:
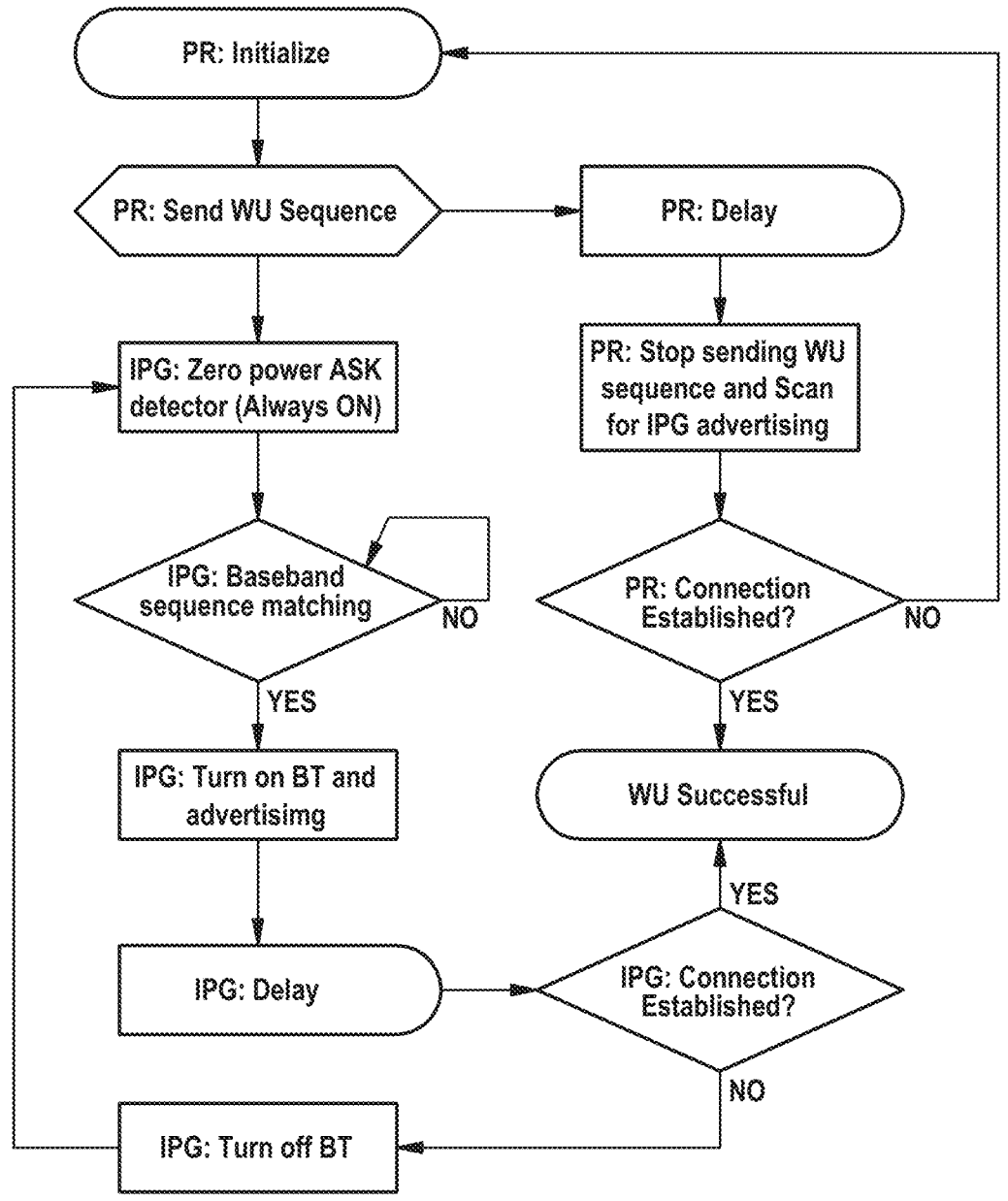
FIG. 7 shows a flow chart of a wake-up protocol in accordance with one or more embodiments.

FIG. 7 shows a flow chart of a wake-up (WU) protocol in accordance with, e.g., the embodiment described above with reference to FIGS. 5 and 6. In this exemplary embodiment, the external device 2 is referred to as a patient remote (PR), whereas the implantable medical device 1 is referred to as an implantable pulse generator (IPG).

The patient remote PR initializes the wake-up procedure and sends a wake-up sequence in the form of an ASK modulated wake-up signal W1. After a programmable delay, the patient remote PR stops sending the wake-up sequence and starts scanning for an advertising message from the implantable pulse generator IPG.

In the meantime, the wake-up sequence is received and demodulated by the always on ASK demodulator circuitry 11 ("Zero power ASK detector (Always ON)") of the implantable pulse generator IPG. A demodulated wake-up signal W2 is transferred from the demodulator circuitry 11 to the match detector circuitry 14 of the implantable generator IPG for verification ("Baseband sequence matching"). In case of a successful verification, the awake state of the implantable pulse generator IPG is activated. The Bluetooth communications transceiver circuitry 15 of the implantable pulse director IPG is then turned on and starts advertising by transmitting advertising messages. Such an advertising message may be received by the patient remote PR, which is in scan mode.

If the implantable pulse generator IPG determines after a programmable delay that a connection with the patient remote PR has been established, it considers the wake-up successful. In the alternative, if the implantable pulse director IPG determines that no connection has been established within the programmable delay period, the Bluetooth communications transceiver circuitry 15 is turned off again until the ASK demodulator circuitry 11 receives the next valid modulated wake-up signal W1.

Likewise, if the patient remote PR determines that a connection with the implantable pulse generator IPG has been established, it considers the wake-up successful. In the alternative, the patient remote PR initializes the wake-up procedure once again and the wake-up procedure starts from the beginning.

Referring now again to FIG. 4, within the implantable medical device 1 a multiplicity of signals may be defined which may be used by the external device 2 for waking up the implantable medical device 1. Such signals, denoted in this text as matching signals, are defined in the implantable medical device 1, for example, according to their characteristics, such as pulse durations t0, t1, t2, t3 of pulses of an advertising sequence and an interval T1 by which groups of pulses are periodically repeated within the advertising sequence. Multiple different matching signals herein may be defined within the implantable medical device 1, the different signals differing, e.g., in the combination of used pulses having pulse durations t0, t1, t2, t3 and in the repetition interval T1.

If the external device 2 broadcasts a wake-up signal W1 which matches one of the predefined matching signals, the implantable medical device 1, for example in the match detector circuitry 14, identifies the wake-up signal W1 as a valid wake-up signal and correspondingly activates the awake state of the implantable medical device 1.

Herein, it shall be avoided that the implantable medical device 1 is woken up repeatedly by signals which may resemble one of the predefined matching signals but are not emitted from an external device 2 configured and intended for waking up the implantable medical device 1. If the implantable medical device 1 is transferred to its awake state repeatedly, for example, when receiving a signal from a device which resembles a matching signal, but which not truly is a wake-up signal (for example, if a device transmits Bluetooth signal sequences within a Bluetooth communication which closely resembles one of the matching signals, but are not emitted with the intent to wake-up the implantable medical device 1), the repeated activation of the implantable medical device 1 will wear down the device's battery and hence will reduce the operational life span of the implantable medical device 1. This is to be avoided.

For this reason, it herein is proposed to block an activation by a wake-up signal W1 which resembles one of the predefined matching signals if it is found, upon activation of the implantable medical device 1, that the activation is invalid. For example, if upon activation of the communications transceiver circuitry 15 the implantable medical device 1 attempts to establish a communication with the external device 2, but is not able to establish the communication, or in the communication identifies the external device 2 to be not authenticated to wake up the implantable medical device 1, the implantable medical device 1 again is deactivated and hence is transferred to its dormant state. In this case, the matching signal corresponding to the received wake-up signal W1 may be blocked, for example in a list of matching signals corresponding to a block list of those matching signals which subsequently shall not be usable for waking up the implantable medical device 1.

The blocking may be achieved by including the particular matching signal (corresponding to the wake-up signal W1 for which the activation has been identified as invalid) in the (block-)list of matching signals. The blocking may be established after a first reception and erroneous activation of the implantable medical device 1. Alternatively, the blocking may be established only if within a predefined time span a predefined number of receptions and erroneous activations take place, for example within a time span of multiple minutes, for example between 5 minutes and 10 minutes.

As a consequence of the blocking, the implantable medical device 1 is not activated if subsequently a wake-up signal W1 is received which resembles the particular, blocked matching signal as identified in the (block-)list of matching signals.

The blocking may be valid, for example, for a predefined time duration, such that after the predefined time duration the matching signal again is removed from the (block-)list of matching signals, and after lapse of the time duration hence the implantable medical device 1 may again the woken up by a wake-up signal W1 resembling the particular matching signal. In one embodiment, the time duration which a wake up sequence stays on the block list increases each time a wake-up signal is returned to the block list after having been removed from it. For example, the first time a wake-up signal is put on the block list it may be for 1 hr, if it is put on the block list again within a 24 hr period, the second time it will be put on the block list for 4 hrs. If it is put on the block list a $3^{rd}$ time within 24 hrs, it will be added to the block list for a full 24 hrs. In this way the implant minimizes the energy it spends on repeated false wake-ups.

In the unlikely event that the number of matching signals included in the (block-)list of matching signals becomes large, for example if all predefined matching signals are included in the list, it may occur that an activation of the implantable medical device 1 is no longer possible. If this is unacceptable, certain mitigations may be implemented.

For example, if it is found that the number of matching signals included in the (block-)list exceeds a predefined number, for example a number larger than 50% of the predefined matching signals, one or multiple matching signals may be removed from the (block-)list, for example on a first on/first off basis or on a random basis, such that the number of block-listed matching signals on the list is reduced.

For example, one or multiple matching signals may be removed from the (block-)list if it is found that all matching signals are included in the list. In this case, for example, one or multiple matching signals which are in the list the longest may be removed from the list, such that matching signals become available for activating the implantable medical device 1.

In another embodiment, a time duration, for which an activation based on a matching signal included in the (block-)list is blocked, may be shortened. For example, regularly a matching signal may remain on the (block-)list for a predefined time duration. If it is found that an excessive number of matching signals is included in the (block-)list, for example all matching signals, the time duration for one or multiple matching signals may be shortened, such that matching signals are removed from the list faster.

For waking up the implantable medical device 1, the external device 2 may be designed such that it cycles through wake-up signals according to the available matching signals. Hence, the external device 2 may use different wake up signals W1 to attempt to wake-up the implantable medical device 1.

The set of matching signals may be defined in an initial training phase. For example, the control circuitry 16 of the implantable medical device 1 may implement a training mode in which a state machine is used to measure parameters, such as pulse durations t0, t1, t2, t3 and an interval T1 of training wake-up signals received from the external device 2. According to the measurements, matching signals may be defined within the implantable medical device 1 and may be usable subsequently in operation for waking up the implantable medical device 1. This allows, for example, smartphone from multiple manufactures and with multiple different operating systems to all have an app that can through training wake up the implantable medical device.

The training may be repeated, for example in case of an update of an operating system of the external device 2, such that matching signals may be defined anew.

A training may, for example, be performed at an initialization of the implantable medical device 1, for example using a coil link communication, for example during a pairing/bonding process in which a communication with an external device 2 is initially set up.

In one embodiment, the control circuitry 16 is adaptive in that it may adaptively change matching signals defined in the implantable medical device 1. For example, in one embodiment, in case of a successful activation of the implantable medical device 1 and in case of a successful establishment of a communication with the external device 2, the matching signal used by the external device 2 may be included in a safelist to indicate that the particular matching signal previously has been identified as a valid wake-up signal leading to a successful, valid activation of the implantable medical device 1.

For matching signals included in the safelist, e.g., a weighing parameter may be increased. An inclusion of a matching signal in the blocklist in contrast may cause a reduction of the weighing parameter. Based on the weighing parameter, for example, a time duration for which a matching signal is blocked may be set in case a wake-up signal corresponding to a matching signal is received leading to a false, invalid activation of the implantable medical device 1.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE SIGNS

1 Implantable medical device
10 Power supply
11 Demodulator circuitry
12 Antenna
13 Frontend matching circuitry
14 Match detector circuitry
15 Communications transceiver circuitry
16 Control circuitry
2 External device
3 System
D Diode
E1-E8 Events
L Inductor
R Resistor

19

S1, S2, S3 Method steps
S/W Software
t0, t1, t2, t3 Pulse durations
T1 Interval
W1 Modulated wake-up signal
W2 Demodulated wake-up signal
W3 Logical wake-up signal
The invention claimed is:

1. A method for waking up an implantable medical device from a dormant state, the method comprising:
sending a wake-up signal via a wireless link by means of an external device;
receiving the wake-up signal by the implantable medical device in the dormant state;
activating an awake state of the implantable medical device in response to the wake-up signal;
attempting with at least one or a predefined number of attempts, in the awake state of the implantable medical device, to establish a communication between the external device and the implantable medical device;
identifying, by the implantable medical device, the activation of the awake state as a valid activation based on the attempting to establish a communication;
in case the activation of the awake state is not identified as a valid activation, blocking a subsequent activation of the awake state of the implantable medical device based on the wake-up signal, wherein said blocking includes: marking a predefined matching signal corresponding to the wake-up signal as invalid in a list of matching signals so that a signal is received by the implantable medical device which resembles a matching signal as identified in the list of matching signals, the implantable medical device is not transferred to the awake state; and
if, during the identifying, it is detected that the list of matching signals includes a number of predefined matching signals equal to or exceeding a predefined maximum number, modifying the list of matching signals by marking at least one matching signal of the list of matching signals as valid.

2. The method according to claim 1, wherein said receiving includes: processing, by the implantable medical device, the wake-up signal to identify the wake-up signal as a valid wake-up signal by comparing the wake-up signal to a predefined matching signal.

3. The method according to claim 2, wherein the processing includes: deriving information from the wake-up signal and comparing said information to a predefined set of information representative of the predefined matching signal to identify the wake-up signal as a valid wake-up signal.

4. The method according to claim 3, wherein the wake-up signal is identified as a valid wake-up signal if the derived information matches a predefined set of information out of a multiplicity of sets of information representative of a group of predefined matching signals.

5. The method according to claim 3, wherein said predefined set of information includes at least one of a pulse duration and an interval, the wake-up signal being formed by the external device according to a sequence of groups of transmission pulses, each transmission pulse having a specified pulse duration and the groups of transmission pulses being repeated at a specified interval.

6. The method according to claim 1, wherein said blocking includes: preventing an activation of said awake state of the implantable medical device based on the wake-up signal for a predefined time duration.

7. The method according to claim 1, including: if, during the identifying, it is detected that the list of matching signals includes a number of wake-up signals equal to or exceeding a predefined maximum number, decreasing a value of a predefined time duration, during which an activation of the awake state of the implantable medical device is blocked for a particular matching signal, for at least one matching signal of the list of matching signals.

8. The method according to claim 1, wherein said sending by the external device includes: sending the wake-up signal as a modulated signal.

9. The method according to claim 1, wherein the sending includes: transmitting the wake-up signal via a Bluetooth interface of the external device.

10. The method according to claim 1, wherein said receiving by the implantable medical device includes: demodulating the wake-up signal by means of a demodulator circuitry of the implantable medical device.

11. An implantable medical device configured to selectively assume an awake state and a dormant state, the implantable medical device comprising:
reception circuitry configured to receive a wake-up signal via a wireless link from an external device;
activation circuitry configured to activate an awake state of the implantable medical device in response to a received wake-up signal;
communication circuitry configured to establish, in the awake state, a communication between the external device and the implantable medical device; and
processing circuitry configured to identify the activation of the awake state as a valid activation based on at least one or a predefined number of attempts to establish a communication, and in case the activation of the awake state is not identified as a valid activation, to block a subsequent activation of said awake state of the implantable medical device based on the wake-up signal, wherein said blocking includes: marking a predefined matching signal corresponding to the wake-up signal as invalid in a list of matching signals so that a signal is received by the implantable medical device which resembles a matching signal as identified in the list of matching signals, the implantable medical device is not transferred to the awake state, wherein if, during the identifying, it is detected that the list of matching signals includes a number of predefined matching signals equal to or exceeding a predefined maximum number, modifying the list of matching signals by marking at least one matching signal of the list of matching signals as valid.

12. The implantable medical device according to claim 11, wherein said communication circuitry is configured to establish a communication according to a Bluetooth protocol.

13. A system, comprising an external device configured to send a wake-up signal via a wireless link; and an implantable medical device according to claim 11.

* * * * *